US00PP12908P2

(12) United States Plant Patent
Towe

(10) Patent No.: US PP12,908 P2
(45) Date of Patent: Sep. 3, 2002

(54) PHLOX PLANT NAMED 'BECKY TOWE'

(76) Inventor: June Towe, Wychwood, Aynall Lane, Little Hereford, Ludlow, Shropshire (GB), SY8 4BA ( * ) Notice: Subject to any disclaimer, the term of this patent is extended or adjusted under 35 U.S.C. 154(b) by 0 days.

(21) Appl. No.: 09/668,843

(22) Filed: Sep. 22, 2000

(30) Foreign Application Priority Data

Nov. 6, 1999 (EP) ..... 1999/1579

(51) Int. Cl.[7] ..... A01H 5/00
(52) U.S. Cl. ..... Plt./320
(58) Field of Search ..... Plt./320

*Primary Examiner*—Bruce R. Campell
*Assistant Examiner*—June Hwu

(57) ABSTRACT

A new cultivar of *Phlox paniculata* named 'Becky Towe' that is characterized by its gold margined variegated foliage that matures to a cream color when in bloom, its bronze growing tips on its spring foliage, its rich salmony carmine-rose colored blooms, and its vigorous growth habit of mildew resistant foliage.

3 Drawing Sheets

BACKGROUND OF THE INVENTION

The present invention relates to a new and distinct cultivar of *Phlox paniculata* and will be referred to hereafter by its cultivar name 'Becky Towe'. *Phlox paniculata* is a hardy perennial grown for landscape use.

The new Phlox, 'Becky Towe', was discovered in April of 1990 by the inventor in her garden in Ludlow, Shropshire, England. 'Becky Towe' was discovered as a golden variegated sport arising from the base of *Phlox paniculata* 'Windsor' (unpatented).

The new variety of Phlox can be characterized by its gold-margined variegated foliage that is bright gold with bronzed growing tips in the spring with the gold margins maturing to a cream color at flowering time. 'Becky Towe' has flowers that are a rich salmony carmine rose color with a deep magenta colored eye, is a vigorous grower, and is comparatively resistant to mildew. The flower color is identical to the parent variety, however, 'Windsor' has green foliage with no variegation. 'Becky Towe' is unique in comparison to other variegated *Phlox paniculata* cultivars. The cultivars 'Norah Leigh', 'Darwin's Joyce', and 'Pink Posie' (all unpatented) all have foliage with cream to white colored margins and pale lilac to pale pink colored blooms. The cultivar 'Harlequin' (unpatented) has foliage with ivory-white margins and reddish purple flowers and the cultivars 'Silvermine' and 'Goldmine' (both unpatented) have golden variegation, however, the flowers are white and red-purple, respectively.

Asexual reproduction of the new cultivar was first accomplished by taking cuttings in Ludlow, Shropshire, England by the inventor in April 1991. The characteristics of this cultivar have been determined to be stable and are reproduced true to type in successive generations both by vegetative cuttings and by tissue culture.

SUMMARY OF THE INVENTION

The following traits have been repeatedly observed and represent the characteristics of the new cultivar. These attributes in combination distinguish this cultivar from other commercial varieties. 'Becky Towe' has not been tested under all possible conditions and phenotypic differences may be observed with variations in environmental, climatic, and cultural conditions:

1. The foliage of 'Becky Towe' is variegated with gold colored margins on active growth that matures to a cream color when the plant is flowering. Scorching of the leaf margins has not been observed.
2. The tips on the new growing shoots of 'Becky Towe' in the spring are bronzed tinged.
3. The flowers of 'Becky Towe' are a rich salmony carmine rose color with a deep magenta colored eye. The flowers are held on sturdy, erect stems.
4. 'Becky Towe' appears to be mildew resistant; possibly because it has a wax-like cuticle layer.
5. 'Becky Towe' is hardy in USDA Zones 4–8.
6. 'Becky Towe' is a vigorous grower; many cultivars of variegated *Phlox paniculata* are weaker growers.

BRIEF DESCRIPTION OF THE DRAWING

Sheet One shows 'Becky Towe' in bloom and shows the foliage coloration at the time of bloom.

Sheet Two shows a close-up of the spring foliage of 'Becky Towe'; the gold margins and the bronze color of the growing tips can be observed.

Sheet Three shows a plant of 'Windsor' in front of containers of 'Becky Towe'. The colors in these photographs are as accurate as possible by conventional photography.

BOTANICAL DESCRIPTION OF THE PLANT

The following is a detailed description of the new cultivar as grown under garden conditions in Plymouth, Minn. The observed plant was in its fourth year of growth. The color determination is in accordance with The R.H.S. Colour Chart of The Royal Horticultural Society, London, England, except where general color terms of ordinary dictionary significance are used.

Botanical classification: *Phlox paniculata* 'Becky Towe'.
Common name: Garden Phlox, Summer Phlox.
Commercial classification: Hardy perennial for landscape use.

Parentage: Sport of *Phlox paniculata* 'Windsor' (unpatented).

Plant description:

*Blooming period*.—Blooms from July–September in S. England, approx 11 weeks.

*Plant habit*.—Upright, clump-forming.

*Height and spread*.—70 cm in height and 50 cm in spread after 3 years under good growing conditions.

*Hardiness*.—Zone 4–8.

*Type*.—Hardy herbaceous perennial.

*Root system*.—Fibrous.

*Culture*.—Fertile, moisture retentive soils in full sun or part shade.

*Diseases and pests*.—Appears to be resistant to powdery mildew as compared to most cultivars, possibly due to the waxy cuticle layer on the leaves. Powdery mildew has not been observed. Susceptible and not resistant to the commonly-occurring pests of cultivars of *Phlox paniculata*, including eelworm and two-spotted mite.

Propagation:

*Methods of propagation*.—Cuttings, tissue culture, division.

*Time required to initiate new roots*.—About 10 days at 20° C. in the spring months and about 12 days at 20° C. during the summer months.

*Time required to develop roots*.—About 28 days at 20° C. in the spring months and about 35 days at 20° C. in the summer months.

*Cropping time*.—About 15 months to produce a finished plant in a gallon container: variable depending on environmental conditions.

Stem description:

*Shape*.—Round.

*Size*.—1.3–3.0 mm in diameter.

*Surface*.—Glabrous.

*Color*.—144A–B.

*Branching*.—None, basal shoots only.

*Internode length*.—1.0–3.0 mm.

Foliage description:

*Shape*.—Elliptic to elliptic-lanceolate.

*Arrangement*.—Leaves simple, opposite.

*Apex*.—Acute-acuminate.

*Base*.—Attenuate, sessile.

*Venation*.—Recessed mid vein, others not prominent.

*Margins*.—Entire, with hand lens observed as very finely toothed with evident roughness when rubbed towards the petiole. Smooth if rubbed away from the petiole.

*Arrangement*.—Decussate.

*Surface*.—Glabrous when mature, glossy when actively growing.

*Size approximately*.—10 cm in length and 3.5 cm in width.

*Color*.—Leaf centers, upper surface, young leaves: 137B–C. Leaf centers, lower foliage, young leaves: 139B. Leaf centers, upper foliage, mature leaves; 137B–C. Leaf centers, lower foliage, mature leaves; 191A. Margins, upper surface, young leaves; varies between 10B and 12B. Margins, lower surface, young leaves; varies between 10D and 12D. Margins, upper surface, mature leaves; 11D. Margins, lower surface, mature leaves; 196B. Intermediate area, upper surface, young leaves; varies between 143C and 145B. Intermediate area, lower surface, young leaves; varies between 139D and 145B. Intermediate area, upper surface, mature leaves; varies between 145B and 148D. Intermediate area, lower surface, mature leaves; varies between 139D and 145B. Young shoot tips; approx. 151A with an overlay of 166A (bronze): color gradually differentiates into the color pattern above, young leaves near the flowers may be almost all gold (young leave foliage colors) with the green centers developing later.

Flower description:

*Type*.—Terminal, compact, corymbiform cymes, salviform corolla.

*Fragrance*.—Sweet.

*Size*.—3.3–3.7 cm in diameter, 2.7–3.1 cm in length.

*Petioles*.—3.0 mm in length.

*Buds*.—Size: length fully developed: 2.0–2.5 cm including tube 0.8 cm; diameter: 2 mm at emergence to 5 mm fully developed. Shape: tubular surmounted by ovate spirally furled cluster. Color:at first emergence about 2 mm in length: 155A, thereafter becoming flushed with 66A prior to unfurling.

*Petals*.—5, apopetalous, overlapping. Size; 1.0–1.3 cm in length, 1.1–1.3 cm in width (middle of petal), eye zone is 1.0 cm in diameter. Shape: rhomboidal; apex, rounded, occasionally rounded-acute, occasionally with tiny notch about 1 mm deep or wide. Margin: entire Surface texture: smooth, satiny; tube pubescent Petal color; 52A–B, eye varies between 66A and 67A, lighter area surrounding eye approx. 62B, perianth tube 64A–B.

*Calyx*.—5, partially synsepalous with flaring tips 3–4 mm in length, persistent, Surface; Glabrous. Size; 6–8 mm in length, 3 mm in width. Sepal color (upper surface): 64A. Lower surface same 64A or slightly darker.

*Reproductive organs*.—Stamens; 5, included, appressed to corolla, apostemonous. Pistil; 1, style trifid at apex, 3 stigmas. Fruit: Ovary is Superior, loculicidal capsule, 3-valved, 0.8 cm in length and 0.5 cm in width, color 164B.

*Seed production*.—None has been observed.

I claim:

1. A new and distinct cultivar of Phlox plant named 'Becky Towe' as described and illustrated.

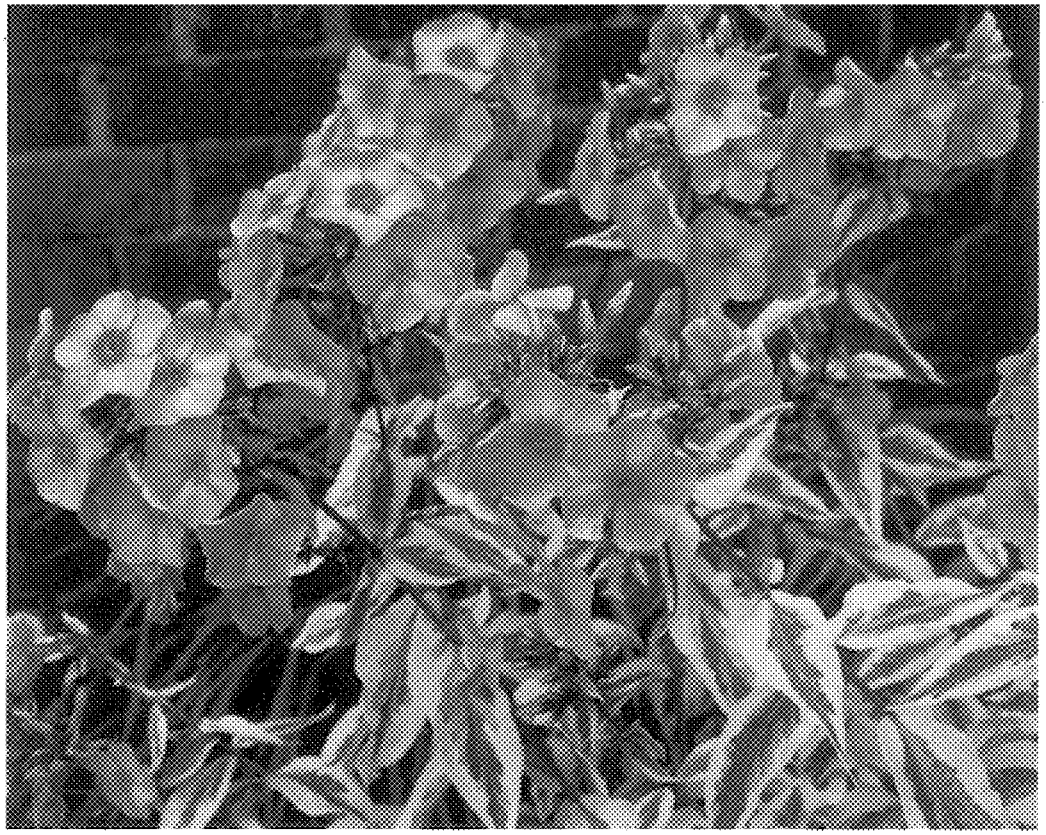

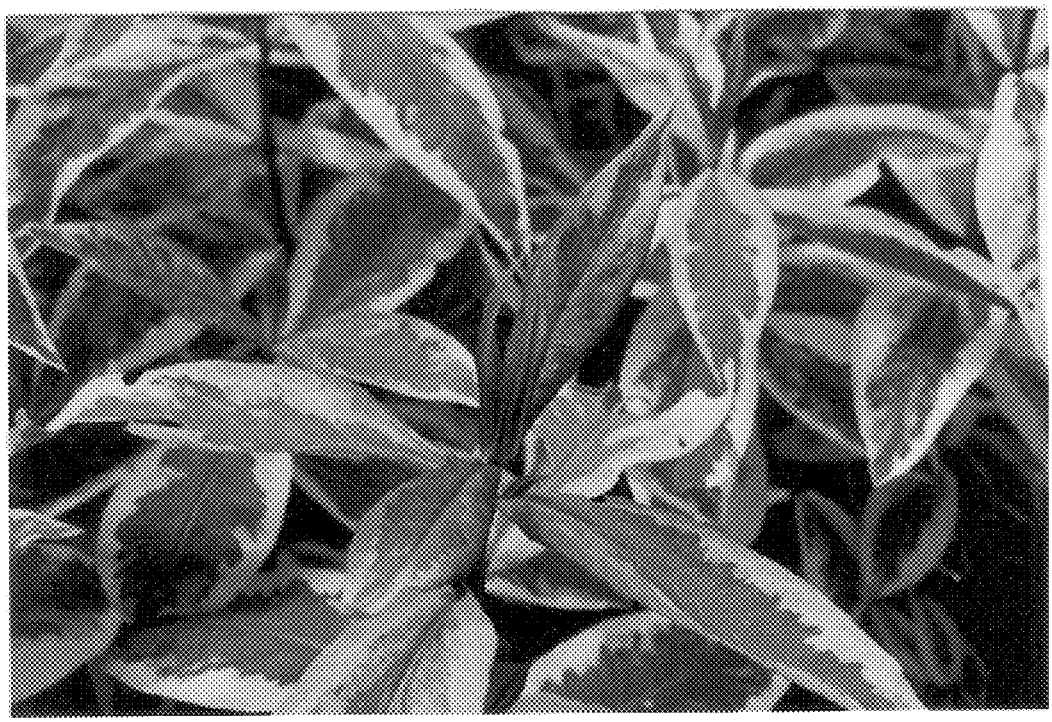

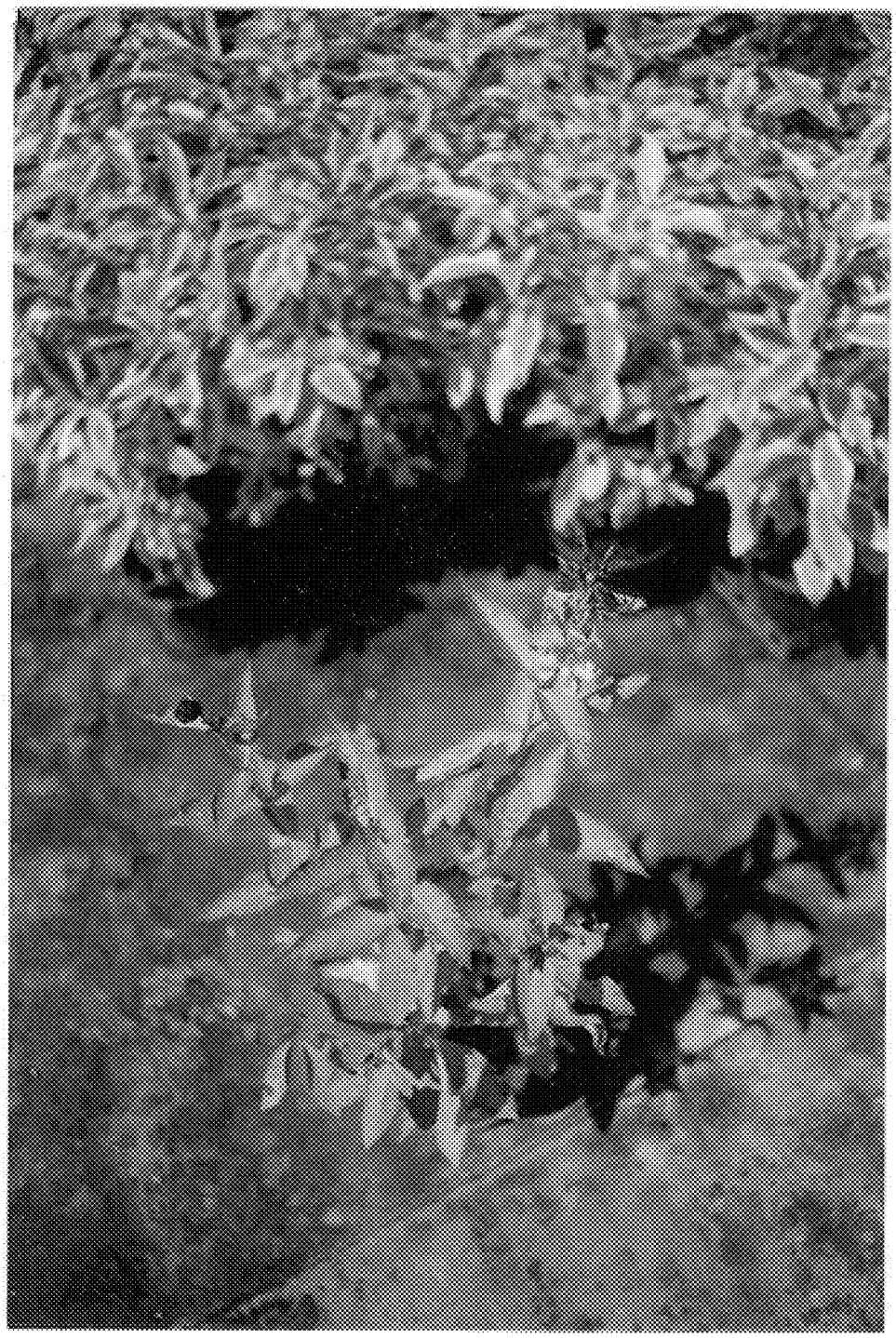

* * * * *